United States Patent [19]

Kirmann

[11] Patent Number: Plant 6,018

[45] Date of Patent: Sep. 22, 1987

[54] GERANIUM PLANT NAMED ROSY

[75] Inventor: Wolfgang Kirmann, Langenzersdorf, Austria

[73] Assignee: Mirko Vavra, Bisamberg, Austria

[21] Appl. No.: 810,742

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Rosy having pale pink flower color, variegated with dark red-purple; floriferous, compact self-branching growth habit; early flowering response; good bud production at night temperatures up to 16° C., thus providing a long and continuous flowering period; good resistance against parasites; and ease of propagation and good rooting habit.

2 Drawing Figures

The present invention comprises a new and distinct cultivar of geranium, botanically known as *Pelargonium domesticum,* and hereinafter referred to by the cultivar name Rosy.

Rosy is a product of a planned breeding program which had the objective of creating new geranium cultivars having good flower production, compact growth habit, very early flowering response and long flowering period, pale pink flower color with dark red-purple variegation.

Rosy was originated from a hybridization made by applicant in a controlled breeding program in Bisamberg, Austria in the spring of 1978. The female parent was a cultivar designated as seedling 300/72 having a very vigorous growth habit and white flower color with lilac colored markings. The male parent of Rosy was a cultivar designated as seedling 41/76, characterized by its compact, floriferous growth habit and lilac flower color.

Rosy was discovered and selected as one flowering plant within the progeny of the stated cross by applicant on Mar. 25, 1979 in a controlled environment in Bisamberg, Austria.

The first act of asexual reproduction of Rosy was accomplished when vegetative cuttings were taken from the initial selection on Aug. 25, 1980 in a controlled environment in Bisamberg, Austria by a technician working under formulations established and supervised by Wolfgang Kirmann. Horticultural examination of selected units initiated in the spring of 1980 has demonstrated that the combination of characteristics as herein disclosed for Rosy are firmly fixed and are retained through successive generations of asexual reproduction.

Rosy has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Rosy, which in combination distinguish this geranium as a new and distinct cultivar.

1. Pale pink flower color, variegated with dark red-purple.
2. Good bud production and very floriferous.
3. Healthy, medium green foliage.
4. Compact, self-branching growth habit.
5. Good resistance against parasites, particularly white fly, an important commercial consideration.
6. Early flowering, continuing through spring and summer due to good flower bud production.
7. Propagates well, with very good rooting habit.
8. Buds are produced under normal greenhouse conditions (5000 Lux for 16 hours per day) at 14°–16° C. This is well above the cooler temperatures required for previous *domesticum* varieties. In addition, plants flowered indoors can be transplanted outdoors and will continue blooming at night temperatures as high as 16° C. Known *domesticum* cultivars will produce buds outdoors only at night temperatures of 10° C. or lower.
9. Rosy is unique with regard to the combined features of compactness, continuous flowering, floriferous habit, and pale pink flower color.

Of the many commercial cultivars known to the present inventor, the most similar in comparison to Rosy is Lavender Grand Slam, an unpatented but commercial cultivar. In comparison to Lavender Grand Slam, Rosy has a more compact growth habit, earlier flowering response and a light pink flower color.

The accompanying photographic drawings show typical flower and foliage characteristics of Rosy, with colors being as true as possible with illustrations of this type.

Sheet 1 is a perspective view of a potted plant of Rosy.

Sheet 2 is a black and white print showing the upper surface of immature and mature plants of Rosy.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

Classification:

*Botanical.—Pelargonium domesticum.*

*Commercial.*—Commonly referred to as a "Martha Washington" geranium, and having the cultivar name Rosy.

INFLORESCENCE

A. Umbel:

*Average diameter.*—Large; 120–125 mm.

*Peduncle length.*—Normal.

*Pedicel length.*—Normal.

B. Corolla:

*Average diameter.*—80–85 mm; total inflorescence diameter within the foliage.

*Form.*—7 petals on first flowering; subsequent flowerings may have fewer petals per flower.

*Color (general tonality from a distance of three meters).*—Pale pink, with wine-red variegation.

*Color (upper surface).*—56D, variegated with 60A.

C. Bud:

*Shape.*—Oval.

*Color.*—Very pale pink; lighter than mature flower.

D. Reproductive organs:

*Androecium.*—Yellow.

*Gynoecium.*—Normal.

E. Spring flowering response period: Early.

F. Durability. Very good.

PLANT

A. Foliage:

*Form.*—Zygomorphic with a nectar spur.

*Margin.*—Crenate.

*Color (upper surface).*—Medium green.

*Tolerance of Botrytis and soil fungi.*—Good.

B. General appearance and form:

*Internode length.*—Short.

*Branching pattern.*—Good.

*Height.*—Compact.

I claim:

1. A new and distinct cultivar of geranium named Rosy, as described and illustrated, and particularly characterized by its pale pink flower color, variegated with dark red-purple; floriferous, compact self-branching growth habit; early flowering response; good bud production at night temperatures up to 16° C., thus providing a long and continuous flowering period; good resistance against parasites; and ease of propagation and good rooting habit.

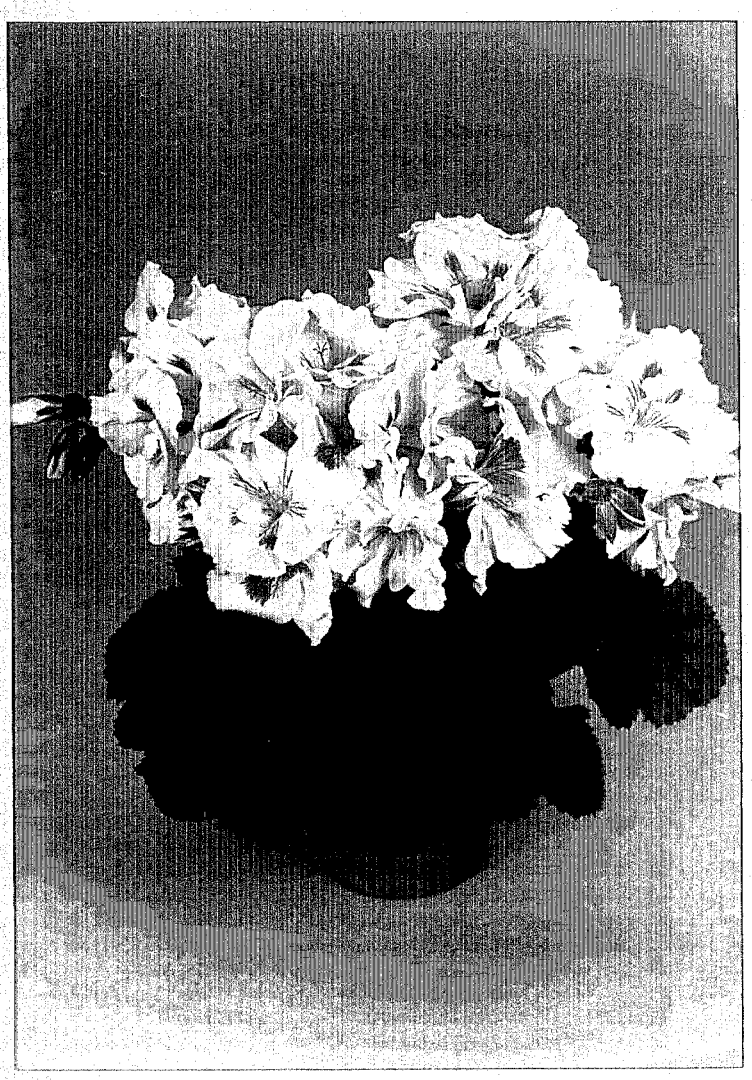

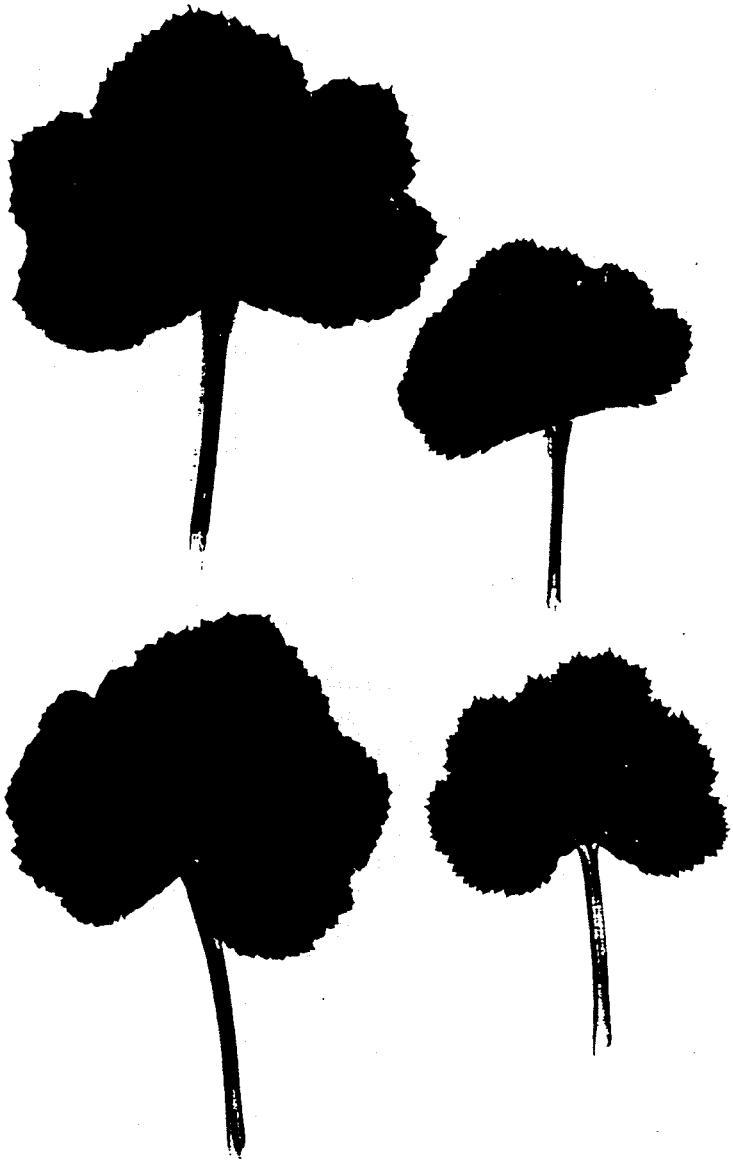

* * * * *